United States Patent [19]

Ikenoue et al.

[11] 4,157,289
[45] Jun. 5, 1979

[54] PROCESS FOR PREPARING SLIGHTLY SOLUBLE SILVER SALT GRAINS

[75] Inventors: Shinpei Ikenoue; Takao Masuda, both of Asaka, Japan

[73] Assignee: Fuji Photo Film Co., Ltd., Kanagawa, Japan

[21] Appl. No.: 903,435

[22] Filed: May 8, 1978

[30] Foreign Application Priority Data

May 6, 1977 [JP] Japan .................................. 52-51872

[51] Int. Cl.$^2$ ......................... B01K 3/00; G03C 1/02; G03C 1/76
[52] U.S. Cl. .............................. 204/195 F; 96/48 HD; 96/97; 96/114.1; 423/491
[58] Field of Search ............ 96/68, 76 R, 94 R, 114.6, 96/97 R, 28, 90 R, 48 HD; 204/1 T, 195 F; 423/491

[56] References Cited

U.S. PATENT DOCUMENTS

| | | | |
|---|---|---|---|
| 3,532,502 | 10/1970 | Boyer et al. | 96/114.6 |
| 3,676,319 | 7/1972 | Kirsten | 204/195 F |
| 3,706,565 | 12/1972 | Ericson | 96/114.1 X |
| 3,770,448 | 11/1973 | Poot et al. | 96/114.1 |
| 3,844,797 | 10/1974 | Willems et al. | 96/114.1 |
| 3,933,508 | 1/1976 | Ohkubo et al. | 96/114.1 |
| 4,002,547 | 1/1977 | Neti et al. | 204/195 F |
| 4,028,129 | 6/1977 | Suzuki et al. | 96/114.1 |

Primary Examiner—Arthur C. Prescott
Attorney, Agent, or Firm—Sughrue, Rothwell, Mion, Zinn and Macpeak

[57] ABSTRACT

A process for preparing slightly soluble silver salt grains by mixing a solution or dispersion of a silver salt forming agent as a first liquid with a solution or dispersion of a silver ion-providing agent as a second liquid while controlling the electrode potential of the mixture of the first liquid and the second liquid using a measuring electrode and a reference electrode to produce the slightly soluble silver halide grains of specific characteristics depending upon the control of the electrode potential, the improvement which comprises the reference electrode comprising an internal electrode of a metal immersed in an internal solution of a metal salt of the metal of the internal electrode and an electrolyte, which metal salt and electrolyte do not release halide ions in the same liquid present as the major component in either of the first liquid or the second liquid.

20 Claims, 2 Drawing Figures

PROCESS FOR PREPARING SLIGHTLY SOLUBLE SILVER SALT GRAINS

BACKGROUND OF THE INVENTION

1. Field of the Invention

The present invention relates to a process for preparing slightly soluble silver salt grains and, more particularly, to a process for preparing slightly soluble silver salt grains by controlling the electrode potential of the reaction solution containing an organic liquid.

2. Description of the Prior Art

Slightly soluble silver salt grains, or silver salt grains insoluble in a reaction solvent or a coating solvent, are often used in the photographic field. Typical examples of such grains are light-sensitive silver halide grains. These silver halide grains are usually prepared by reacting silver nitrate with a halogen ion providing agent in a hydrophilic colloid solution. It is known to change the crystal habit or the particle size distribution of the resulting silver halide grains by controlling, during the reaction, the electrode potential of the reaction solution, for example, the pH or pAg (silver ion concentration), e.g., as disclosed in C. E. K. Mees & T. H. James, *The Theory of the Photographic Process*, 3rd Ed., Chap. 2, Macmillan (1976). Mees et al., supra, discloses that octahedral silver halide grains are obtained with a high pAg value and cubic silver halide grains are obtained with a low pAg value, and that by maintaining the pAg constant the particle size distribution of the resulting silver halide grains can be narrowed, and generation of fog can be prevented by maintaining the pH constant.

A means for measuring the electrode potential of the reaction solution is necessary for controlling the electrode potential of the reaction solution. In preparing light-sensitive silver halides in the hydrophilic colloid solution as described above, a half cell combination is used wherein a calomel electrode or a silver/silver chloride electrode is used as a reference electrode and a glass electrode or a silver electrode is used as a measuring electrode.

However, since these reference electrodes use a potassium chloride aqueous solution or a hydrochloric acid aqueous solution as an internal solution, halogen ions contained in the internal solution react with the silver ion contained in a solution to be measured or a reaction solution, and tend to adversely affect the measured electrode potential.

Grains of silver salts of organic compounds containing an imino group, a mercapto or a thione group, or a carboxyl group (hereinafter referred to as organic silver salt grains) described in U.S. Pat. Nos. 3,094,417, 3,152,904, 3,457,075, Japanese Patent application (OPI) No. 36,020/77 (The term "OPI" as used herein refers to a "published unexamined Japanese patent application"), etc., are illustrative of another type of slightly soluble silver salts to be used in a different photographic field, i.e., in the field of heat-sensitive materials or thermally developable light-sensitive materials. Many of these organic silver salt grains are prepared by dissolving organic silver salt-forming agents (i.e., above-described organic compounds or the non-silver salts thereof) in an organic liquid, adding water thereto to form an oil-in-water emulsion, and reacting the resultant emulsion with an aqueous solution of a silver ion-providing agent such as silver nitrate or a silver-ammine complex salt. Control of the pH or the pAg of the reaction solution during preparation of these organic silver salt grains for the purpose of changing the particle size distribution or the particle form of the grains is not known. However, it might be highly expected that, when the pAg is maintained constant, the particle size distribution of the resulting grains would be narrowed and, when the pH is maintained constant, fog could be prevented. Even if the electrode potential of the reaction solution for producing the organic silver salt grains using the above-described calomel electrode or silver/silver chloride electrode were to be attempted, accurate measurement of the electrode potential would be impossible since silver ion in the reaction solution reacts with halide ion in the internal solution of the reference electrode.

It is known to prepare slightly soluble silver salt particles such as silver halide grains or organic silver salt grains in an organic liquid medium. For example, U.S. Pat. No. 3,713,833 discloses a process of preparing light-sensitive silver halide grains or organic silver salt grains in an organic liquid solution of a vinyl copolymer. Also, U.S. Pat. No. 3,700,458 describes a process for preparing heavy metal salts of organic carboxylic acids in a non-aqueous solvent. However, conducting the reaction while controlling the pH or the pAg of the reaction solution during preparation of the slightly soluble silver salt grains using an organic liquid as a reaction medium is not known. Control of the pH or the pAg cannot be attained by using the above-described calomel electrode or silver/silver chloride electrode as a reference electrode. Because, there is the problem that accurate control of the electrode potential is impossible since the liquid (junction) potential difference between a solution to be measured and an internal solution of the reference electrode increases because the two solutions and different and the indicated electrode potential fluctuates.

SUMMARY OF THE INVENTION

Therefore, an object of the present invention is to provide a process for preparing slightly soluble silver salt grains while accurately controlling the pH or the pAg of a reaction solution containing an organic liquid and, in particular, to provide a process for preparing slightly soluble silver salt grains having the desired particle size distribution and grain form by accurately controlling the pH or the pAg using a reference electrode which enables the electrode potential of the reaction solution to be accurately measured.

A further object of the present invention is to provide a process for preparing slightly soluble silver salt grains while controlling the pH or pAg in an organic liquid medium.

These above objects are achieved by the present invention which provides a process for preparing slightly soluble silver salt grains comprising mixing a solution or dispersion of a silver salt-forming agent as a first liquid (Liquid I) with a solution or dispersion of a silver ion-providing agent as a second liquid (Liquid II), while during the mixing controlling the electrode potential of the mixture of the first and second liquids (mixture of Liquid I and Liquid II) using a measuring electrode and a reference electrode to produce slightly soluble silver halide grains of specific characteristics depending upon the control of the electrode potential with the reference electrode comprising an internal electrode of a metal immersed in an internal solution of a metal salt of the metal of the internal electrode of the reference electrode and an electrolyte and which metal salt and electrolyte do not release halide ions in the same liquid present as the major component in either of the first liquid or the second liquid (Liquid I or Liquid II).

BRIEF DESCRIPTION OF THE ACCOMPANYING DRAWINGS

FIG. 1 shows a cross sectional view of a double junction type reference electrode, as an example of a reference electrode to be used in the present invention. In FIG. 1, numeral 1 designates a reference electrode, 11 an internal solution-support tube, 12 an external solution-support tube, 2 an internal solution, 2' an external solution, 3 an internal electrode, 4 a connector, 5 a bottom connector, 6 and 6' replenishing inlets, and 7 a lead wire.

FIG. 2 shows an illustrative view of an apparatus which can be used for practicing the process of the present invention. In FIG. 2, numeral 1 designates a reference electrode, 21 a reactor, 22 a reaction solution or a synthetic polymer solution or dispersion, 23 a measuring electrode, 24 a potentiometer, 25 and 25' flow rate-adjusting means, 26 and 26' addition tubes, and 27 a stirrer.

DETAILED DESCRIPTION OF THE INVENTION

Figure 1:
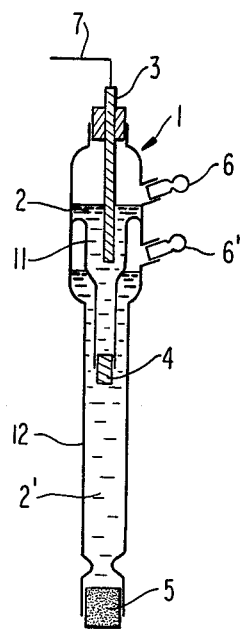

Slightly soluble silver salts which can be prepared by the present invention include all silver salts which can be prepared by adding silver ion and an anion to a reaction medium and which are slightly soluble in the reaction medium. More specifically, examples of such silver salts include light-sensitive silver halides and organic silver salts as described in Japanese Patent Application (OPI) No. 36,020/77.

Specific examples of the above-described light-sensitive silver halides include silver chloride, silver bromide, silver iodide, silver chlorobromide, silver chlorobromoiodide, silver bromoiodide and mixtures thereof.

Examples of the above-described organic silver salts are silver salts of organic compounds having groups capable of forming anions, such as imino groups, mercapto groups or thione groups, or carboxyl groups, etc. More specifically, examples include the following types of organic silver salts.

(1) Silver salts of organic compounds containing an imino group:
  For example, silver salts of benzotriazoles, silver salt of saccharin, silver salts of phthalazinones, silver salts of phthalimides and the like, e.g., as described in U.S. Pat. No. 4,099,039.

(2) Silver salts of organic compounds containing a mercapto group or a thione group:
  For example, silver salt of 2-mercaptobenzoxazole, silver salt of mercaptooxadiazole, silver salt of 2-mercaptobenzimidazole, silver salt of 3-mercapto-4-phenyl-1,2,4-triazole, and the like, e.g., as described in U.S. Pat. Nos. 4,099,039, 3,933,507, 3,785,830, etc.

(3) Silver salts of organic compounds containing a carboxyl group:
  For example, (i) silver salts of aliphatic carboxylic acids such as silver laurate, silver myristate, silver palmitate, silver stearate, silver arachidonate, silver behenate, silver salts of aliphatic carboxylic acids having 23 or more carbon atoms such as silver salts of tricosanoic acid, silver lignocerate and silver pentacosanate, silver adipate, silver sebacate, silver hydroxystearate, etc., e.g., as described in U.S. Pat. Nos. 4,099,039, 3,457,075 or Japanese Patent application (OPI) No. 99,719/75, (ii) silver salts of aromatic carboxylic acids and other carboxylic acids such as silver benzoate, silver phthalate, silver phenylacetate, silver 4'-n-octadecyloxydiphenyl-4-carboxylate, etc., e.g., as described in Japanese Patent application (OPI) No. 99,719/75 and U.S. Pat. No. 4,099,039.

(4) Examples of other silver salts:
  For example, 4-hydroxy-6-methyl-1,3,3a,7-tetrazaindene, silver 5-methyl-7-hydroxy-1,2,3,4,6-pentazaindene, etc., e.g., as described in Japanese Patent application (OPI) No. 93,139/75 or U.S. Pat. No. 4,099,039.

The process of the present invention is suitable for forming slightly soluble silver salts having a solubility product of less than about $10^{-8}$ $(mol/l)^2$ in the reaction medium to be used. Further, the process of the present invention is preferred for forming a silver halide and a silver salt of an aliphatic carboxylic acid, particularly for forming a silver halide using an organic solution as the reaction medium.

These slightly soluble silver salt grains are prepared, in short, by mixing a solution or dispersion prepared by dissolving or dispersing a silver salt-forming agent or a compound capable of reacting with silver ion to provide the desired silver salt (for example, halides, imino compounds, mercapto or thione group-containing compounds, carboxylic acids or the non-silver salts thereof, etc.) in water or an organic liquid (Liquid I), with a dispersion or solution prepared by dispersing or dissolving a silver ion-providing agent (for example, silver nitrate, silver trifluoroacetate, silver tetrafluoroborate, silver perchlorate, etc.) in water or an organic liquid (Liquid II).

In the present invention, the electrode potential of the reaction solution is measured during this mixing using a measuring electrode and a reference electrode to be described hereinafter, and the reaction is conducted while adjusting the mixing rate so as to increase or decrease the potential according to a predetermined value or to maintain the potential at a certain level during the reaction, thus slightly soluble silver salt grains being prepared.

The reference electrode to be used in the present invention employs, as a solvent for the internal solution, a liquid of the same composition as the liquid used for either the solution or dispersion of the above-described silver salt-forming agent to be measured or the solution or dispersion of the above-described silver ion-providing agent, or employs the same liquid as the liquid present in the major proportion in the solvent used in either solution or dispersion, adding at least a soluble metal salt which corresponds to the metal of the internal electrode of the reference electrode and which does not release halide ion, and immersing the internal electrode in the internal solution of the electrode.

The reference electrode which can be used in the present invention may be a single junction type or a double junction type electrode. However, reference electrodes of a double junction type shown in FIG. 1 are particularly effective for continuously measuring the electrode potential over a long period of time, since the internal solution is less contaminated with the reaction solution.

In the present invention the electrode potential of the reaction solution is measured by contacting the above-described internal solution of the reference electrode with the reaction solution to be measured via a connector which does not prevent migration of ions therebetween and by connecting the measuring electrode and the internal electrode of the reference electrode via a potentiometer using an electrical conductor such as a copper wire or the like.

In FIG. 1, reference electrode 1 is separated into internal solution-support tube 11 and external solution-support tube 12, in which internal solution 2 and external solution 2', respectively, as illustrated, are retained. The electrode may be filled with solutions through replenishing inlets 6 and 6' provided at the side of each of the tubes. Ground glass or Teflon stoppers can be advantageously used as stoppers for replenishing inlets 6 and 6', since they are not damaged by internal solution 2 or external solution 2' as compared with rubber stoppers or the like. Internal electrode 3 is immersed in internal solution 2. Internal solution 2 and external solution 2' are connected to each other via connector 4 made of a material which does not prevent migration of ions therebetween. It is also possible to connect these two solutions by making pinholes in the internal solution-support tube. At the bottom of external solution-support tube 12 which is immersed into the reaction solution to measure the potential is provided bottom connector 5 made of a material not preventing migration of ions between the external solution 2' and the solution to be measured. Advantageous materials for connector 4 and bottom connector 5 are ceramic chips and glass frit.

The external solution 2' described above may be the same as internal solution 2. However, a solution having the same composition as the composition of internal solution 2 except for the "metal salt of the metal of the internal electrode" is preferred.

Metals, preferably metals which are difficultly oxidized, particularly preferably metals having a lower ionization tendency than that of hydrogen, can be used as the internal electrode descrobed above. In some cases, metals whose surfaces have been converted to the oxide or the sulfide thereof can be used. In the present invention, silver, palladium, gold or platinum can be used as the internal electrode, with silver, silver sulfide or silver oxide being preferred as the internal electrode. Of these, silver is particularly preferred. The form of the electrode is not particularly limited, and the electrode may be in the form of, for example, rods, plates, wires, etc.

A soluble metal salt of the metal of the internal electrode is incorporated in the internal solution of the reference electrode to be used in the present invention. For example, where silver, silver sulfide or silver oxide is used as an internal electrode, silver salts soluble in the solvent of the internal solution are used. The above-described metal salts must be soluble to some extent in the solvent of the internal solution and ionize to form metal ions. Since the concentration of the metal ion does not necessarily need to be very high, the solubility of the metal salt in the solvent of the internal solution may be low. For example, a solubility of $10^{-6}$ mol/l or more is sufficient. Therefore, the most important factor in selecting suitable metal salts is to select those which do not release halide ions when they are dissolved in the solvent of the internal solution. More specifically, illustrative examples include nitrates, perchlorates, acetates, sulfates, etc. Of these, nitrates and perchlorates are preferably used. Perchlorates are particularly preferred where an organic solvent is used as the reaction medium because of the high solubility of perchlorates in organic solvents. Further, where silver, silver sulfide or silver oxide is used as an internal electrode, silver nitrate or silver perchlorate is preferably used, and silver perchlorate is most preferred.

The mixing proportion of the metal salt of the metal of the internal electrode with the solvent of the internal solution may be varied as desired. However, in general, the mixing proportion of the metal salt ranges from about $10^{-5}$ to about 1 mol/l, preferably from about $10^{-4}$ to about $10^{-1}$ mol/l.

An electrolyte is also added to the above-described internal solution, since the presence of the electrolyte improves the accuracy in measuring the electrode potential and improves the stability. Those electrolytes which are soluble in the solvent of the internal solution, preferably with a solubility of $10^{-3}$ mol/l or more, can be used. On the other hand, electrolytes which can be used must not release halide ions when dissolved in the solvent of the internal solution. Specific examples of electrolytes which can be used include salts of metals having a higher ionization tendency than that of hydrogen (for example, salts of K, Na, Li, Mg, Ca, Rb, Cs, Sr, etc.), onium salts (for example, ammonium, tetra-n-propylammonium, tetraethylammonium, etc., salts), and, in particular, the nitrates or perchlorates thereof. Of these, sodium nitrate, potassium nitrate, calcium nitrate, lithium nitrate, etc., are preferred. In particular, calcium nitrate is useful since it has a good solubility in organic liquids.

The amount of electrolyte which can be used ranges from about $10^{-1}$ to about $10^4$ mols, preferably from 0.2 mol to $10^3$ mols, per mol of the metal salt of the metal of the internal electrode. The concentration of the electrolyte in the solvent of the internal solution may be varied as desired, but, in general, a suitable concentration ranges from about $10^{-6}$ to about $10^4$ mol/l, preferably from about $2 \times 10^{-5}$ to about $10^2$ mol/l. Therefore, the metal salt of the metal of the internal electrode and the electrolyte added to the internal solution may partly be precipitated, although a concentration of a saturated solution or less is preferably used.

Since the internal solution of the reference electrode which is used in the present invention does not contain halide ions, disadvantageous reactions with a solution to be measured or with a solution wherein slightly soluble silver salts are formed are not a problem. Further, since the same solvent as the solvent which is a major component of the reaction solvent for the reaction solution for forming slightly soluble silver salts is used as the solvent for the internal solution, less liquid potential difference exists between the solution whose potential is to be measured and the reference electrode.

In the above-described and following description, the term "organic liquid" is used to describe compounds mainly comprising carbon atoms and hydrogen atoms, and, in some cases, containing oxygen atoms, sulfur atoms or nitrogen atoms, and having a boiling point of about 165° C. or less, preferably about 90° C. or less. More specifically, suitable classes of organic liquids which can be used include alcohols, ketones, aromatic hydrocarbons, aliphatic unsaturated hydrocarbons, ethers, esters, cycloaliphatic hydrocarbons, etc.

Suitable alcohols which can be used include saturated aliphatic alcohols such as methyl alcohol, ethyl alcohol, propyl alcohol, isopropyl alcohol, butyl alcohol, isobutyl alcohol, sec-butyl alcohol, tert-butyl alcohol, amyl alcohol, isoamyl alcohol, hexyl alcohol, etc.; unsaturated aliphatic alcohols such as allyl alcohol, crotyl alcohol, propargyl alcohol, etc.; alicyclic alcohols such as cyclopentanol, cyclohexanol, etc.; aromatic alcohols such as benzyl alcohol, cinnamyl alcohol, etc.; heterocyclic alcohols such as furfuryl alcohol, etc.; and the like.

Suitable ketones which can be used include saturated aliphatic ketones such as acetone, methyl ethyl ketone, methyl propyl ketone, methyl isopropyl ketone, methyl butyl ketone, methyl isobutyl ketone, pinacolone, butyrone, diisopropyl ketone, etc.; unsaturated aliphatic ketones such as methyl vinyl ketone, mesityl oxide, methyl heptenone, etc.; alicyclic ketones such as cyclobutanone, cyclopentanone, cyclohexanone, etc.; aromatic ketones such as acetophenone, propiophenone, butyrophenone, etc.; and the like.

Illustrative esters which can be used are carboxylic acid esters and the like. Preferred carboxylic acids in the carboxylic acid esters are organic carboxylic acids having 1 to 12 carbon atoms and examples include saturated aliphatic carboxylic acids, unsaturated aliphatic carboxylic acids, aromatic carboxylic acids, etc. Examples of alcohols in the esters are preferably alcohols having 1 to 10 carbon atoms, with aliphatic alcohols being particularly preferred. The alcohols may be monohydric or polyhydric. An example of a suitable polyhydric alcohol is glycerin.

Specific examples of the esters described above and which can be used are methyl formate, ethyl formate, propyl formate, isobutyl formate, n-amyl formate, isoamyl formate, isoamyl acetate, methyl acetate, ethyl acetate, isopropyl acetate, butyl acetate, isobutyl acetate, n-amyl acetate, methyl propionate, ethyl propionate, propyl propionate, isopropyl propionate, butyl propionate, isobutyl propionate, n-amyl propionate, isoamyl propionate, methyl butyrate, ethyl butyrate, isopropyl butyrate, methyl isobutyrate, ethyl isobutyrate, butyl isobutyrate, isoamyl isobutyrate, methyl isovalerate, ethyl isovalerate, propyl isovalerate, isopropyl isovalerate, methyl benzoate, butyl phthalate, ethylene glycol monoacetate, acetine, propionine, methyl acrylate, ethyl acrylate, methyl methacrylate, isopropyl methacrylate, etc.

Suitable ethers which can be used are saturated aliphatic ethers such as diethyl ether, dipropyl ether, diisopropyl ether, dibutyl ether, diisobutyl ether, methyl isopropyl ether, methyl butyl ether, methyl isobutyl ether, methyl n-amyl ether, methyl isoamyl ether, ethyl propyl ether, ethyl isopropyl ether, ethyl butyl ether, ethyl isoamyl ether, etc.; unsaturated aliphatic ethers such as diallyl ether, methyl allyl ether, ethyl allyl ether, etc.; aromatic ethers such as anisole, phenetole, diphenyl ether, etc.; cyclic ethers such as trimethylene oxide, tetrahydrofuran, tetrahydropyran, dioxane, etc.; and the like.

Suitable unsaturated aliphatic hydrocarbons which can be used are straight chain, branched chain and cyclic unsaturated aliphatic hydrocarbons such as cyclohexene, dodecene, cycloheptene, cyclopentadiene, cyclopentene, cycloheptadiene, cyclooctatetraene, cyclohexadiene, decene, tetradecene, etc.

Examples of aromatic hydrocarbons which can be used are benzene, toluene, xylene, indene, tetralin, etc.

In addition, cycloalkanes such as cyclooctane, cyclohexane, cycloheptane, cyclopentane, etc., and liquids containing a nitrogen atom or a sulfur atom such as acetonitrile, dimethyl sulfoxide, dimethylformamide, dimethylacetamide, etc., are also suitable.

In the most preferred embodiment of the present invention, slightly soluble silver salt grains are produced using the organic liquids described above as reaction solvents. That is, in preparing slightly soluble silver salt grains by mixing an organic liquid solution of a silver salt-forming agent (Liquid I) with an organic liquid solution of a silver ion-providing agent (Liquid II), the electrode potential of the reaction solution (mixed solution) is measured during the mixing using the reference electrode as described above and the mixing rate is adjusted so as to change the measured potential according to a given value, thus slightly soluble silver salt grains having a definite particle size distribution and a crystal habit determined by this value being obtained.

Except for the measurement of the electrode potential of the reaction solution as described above for this invention, the reactants and reaction conditions which can be employed in the present invention may be the same as conventional reactants and conventional reaction conditions used.

In preparing a light-sensitive silver halide, the above-described silver salt-forming agent means a halogen ion providing agent and, specifically, examples include inorganic halides, halogen-containing metal complexes, onium halides, halogenated hydrocarbons, N-halo compounds, etc., e.g., as described in U.S. Pat. No. 4,099,039. Also, in preparing organic silver salts, examples of silver salt-forming agents (or organic silver salt-forming agents) include organic compounds corresponding to those in the above-described organic silver salts, or the alkali metal salts (e.g., the sodium salts, the potassium salts) of these organic compounds or ammonium salts of these organic compounds as described in U.S. Pat. No. 4,099,039. Further examples of silver ion-providing agents are silver compounds more easily soluble than the slightly soluble silver salts to be produced, such as silver nitrate, silver trifluoroacetate, silver tetrafluoroborate, silver perchlorate, etc.

The concentration used in each of Liquid I or Liquid II described above may be varied as desired but, usually, a suitable concentration is from about $10^{-2}$ wt% to about $10^2$ wt%, preferably from about 1 wt% to about 50 wt%, based on the weight of the organic liquid used.

Upon mixing Liquid I with Liquid II, the presence of an organic liquid solution or dispersion of a synthetic polymer such as those described in U.S. Pat. Nos. 3,713,833 or 3,700,458, is advantageous, since the presence of the synthetic polymer improves the dispersibility of the slightly soluble silver salt grains obtained. Of these synthetic polymers, a hydrophobic synthetic polymer can be particularly advantageously used in the present invention. Specific examples of suitable synthetic polymers which can be used are vinyl copolymers comprising repeating units containing a thioether moiety and alkyl acrylate repeating units, preferably those having a molecular weight of about 10,000 to 50,000 and a solubility in acetone at 25° C. of at least 3 wt%, as well as polyvinyl acetals (e.g., polyvinyl butyral), particularly polyvinyl acetals produced by the reaction of an aldehyde containing 2 to 12 carbon atoms with polyvinyl alcohol and having a polymerization degree of about 100 to about 3,000, preferably 200 to 1,500, and an acetalation degree of more than 50 mol%, preferably more than 60 mol%.

The addition of Liquid I and Liquid II at the same time to a reaction vessel is called a double jet process, whereas the addition of one of Liquid I or Liquid II to the other of Liquid I or Liquid II for mixing is called a single jet process. Either of these processes may be used in the present invention. Where the above-described polymer solution or dispersion is used, this solution or dispersion is previously placed in a reactor.

The reaction temperature can be varied over a wide range. Preferably, the temperature is in the range of from about 0° C. to about 80° C., but less than the boiling point of the reaction medium, more preferably from more than room temperature to 80° C. The reaction temperature can be changed within this range during the reaction, if desired.

The reaction is preferably conducted with stirring. Suitable stirring conditions cannot be described unequivocally, since they will vary depending upon the volume and shape of the reactor used, the shape of the agitating blades, etc. Usually, however, the stirring velocity preferably ranges from about 200 rpm to about 10,000 rpm.

In this invention, the solvent for Liquid I and the solvent for Liquid II, and the solvent for the above-described polymer solution or dispersion, if such is present, may be the same or different, and further a mixture of two or more solvents may be used for Liquid I, Liquid II and the polymer solution or dispersion. However, the respective solvents used and, if two or more organic liquids are used, the solvents must be compatible with each other. It is most preferred for the above-described respective organic liquids to be the same.

Therefore, in the reference electrode to be used in this invention, an organic solvent containing the same organic liquid as one of the solvents used for the above-described Liquids I and II and for the polymer solution or dispersion, if used in some cases, is used as a solvent of the internal solution. Where one of the above-described solvents contains two or more organic liquids, the same liquid as the organic liquid which is a major component, e.g., in an amount of more than 50% by weight, of the composition is satisfactorily used.

In another embodiment of the present invention, the electrode potential of the reaction solution is measured during mixing an oil-in-water emulsion solution of an organic silver salt-forming agent with an aqueous solution of a silver ion-providing agent, and the mixing rate is adjusted so as to change the measured potential according to a predetermined value to conduct the reaction.

Known processes for preparing an oil-in-water emulsion of an organic silver salt-forming agent can be used in this embodiment, such as that described in Japanese Patent Application (OPI) No. 57,111/77, etc. It is preferred for polyvinyl acetal to be present during the mixing, as described in Japanese Patent application No. 133,692/75. Other parameters such as mixing manner, reaction temperature, etc., may be those conditions conventionally used.

In this embodiment, measurement of the electrode potential of the reaction solution can be attained by using water as an internal solution of the reference electrode.

Figure 2:
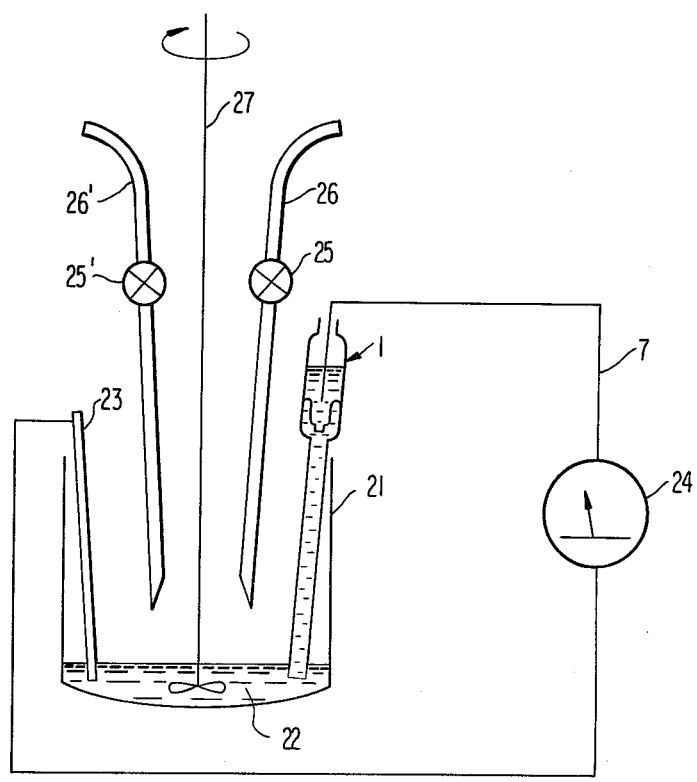

Measurement of the electrode potential of the reaction solution in the present invention can be effected using known procedures and known equipment except for the reference electrode. More specifically, as is shown in FIG. 2, reference electrode 1 and measuring electrode 23 are immersed in the reaction solution while it is mixed or in polymer solution 22 inside reactor 21, and the two electrodes are connected to each other with a lead wire via potentiometer 24. Electrode potentials which are measured in the present invention include pH and pAg (silver ion concentration). Of these, pAg has a marked relationship to the crystal habit, the particle size distribution, various properties (e.g., photographic properties), etc., and hence it is most preferred to measure and control the pAg.

A selective ion sensitive electrode can be used as the above-described measuring electrode. For example, a glass electrode is preferably used for measuring the pH, whereas a silver rod, a silver plate or a like silver electrode is preferably used for measuring the pAg.

The above-described potentiometer indicates the potential itself and not the pH nor the pAg. In order to convert this potential value to pH or pAg, a calibration curve is previously prepared. However, since the pH or the pAg can be controlled by controlling the potential itself, it is usually not necessary to convert the potential value to pH or pAg using a calibration curve. For reference, when the silver potential of the reaction solution is 0 mV, the pAg is 3, and the pAg changes by 1 full unit with change of 59 mV in the silver potential.

In the present invention, to control the electrode potential of the reaction solution according to a predetermined value means to change the electrode potential of the reaction solution according to an optionally predeterminable potential value with time from the time of reaction-initiation (mixing-initiation time) to reaction-completion (mixing-completion time), which includes maintaining the electrode potential at a definite level from the initiation of the reaction to the completion thereof and to change the electrode potential of the reaction solution during the reaction. The pAg is preferably controlled within the range of from 15 to 3, particularly from 12 to 5, in producing silver halides and in the range of from 12 to 2, particularly from 10 to 4, in producing organic silver salts. Particularly, it is preferred to set the pAg at a certain value within the above-described range during the reaction, which results in grains with a narrow particle size distribution being produced.

Control of the electrode potential of the reaction solution according to a predetermined value is attained by increasing or decreasing the rate of mixing the above-described solution of dispersion of a silver salt-forming agent with the solution or dispersion of a silver ion-providing agent, that is, by controlling the addition rate of either or both of the two solutions or dispersions described above, e.g., as shown in FIG. 2, to reactor 21 via pipe 26 and/or 26' through known flow rate adjusting means 25 and/or 25', for example, an orifice, an addition apparatus driven by air pressure, a pump whose rotation rate can be adjusted, a valve, etc.

Known variations such as addition of additives as described in British Pat. No. 1,378,743, Japanese Patent application (OPI) Nos. 22,430/76, 116,024/75, 134,421/75, 88,216/75, 120,715/75, 4,821/77, 41,519/75, 69,628/76, etc., during preparation of slightly soluble silver salt grains or use of ultrasonic waves as described in British Pat. No. 1,408,123, etc., can also be used in the present invention.

According to the process of the present invention, slightly soluble silver salt grains are prepared while controlling the electrode potential of the reaction solution measured by using a reference electrode in which the internal solution thereof does not contain halide ions. Hence undesirable reactions between the reaction solution and the internal solution do not occur and a fluctuation of the indicated potential does not occur. Therefore, the potential can be measured with accuracy.

The process of the present invention enables the electrode potential of the reaction solution to be measured accurately during preparation of slightly soluble silver salt grains using an organic liquid or liquids as the reaction medium or the reaction is conducted in the presence of the synthetic polymer solution or dispersion, thus enabling slightly soluble silver salt grains having the desired particle size distribution, shape and property to be produced by controlling the measured electrode potential of the reaction solution.

The process of the present invention while maintaining the pAg value constant is particularly advantageous for obtaining monodisperse type slightly soluble silver salt grains in an organic liquid as a reaction medium.

The present invention will now be illustrated in more detail by reference to the following non-limiting examples and comparative examples. Unless otherwise indicated herein, all parts, percents, ratios and the like are by weight.

EXAMPLE 1

Preparation of silver bromide using ethanol as a reaction solvent

As illustrated in FIG. 1, a silver rod as an internal electrode 3, ceramic chips as a connector 4 and a bottom connector 5, an ethanol solution of $10^{-2}$ mol/l of $AgClO_4$ and $10^{-1}$ mol/l of $Ca(NO_3)_2$ as an internal solution 2, and an ethanol solution of $10^{-1}$ mol/l of $Ca(NO_3)_2$ as an external solution 2' were used to prepare a reference electrode.

This reference electrode was connected to a silver rod as a measuring electrode via a potentiometer, HM-18B (made by Toa Denpa Co., Ltd.) as shown in FIG. 2. When these respective electrodes were immersed into an ethanol solution containing $10^{-4}$ mol/l of $AgClO_4$, the potentiometer indication was 0 mV. The respective electrodes were immersed into 300 ml of a 5 wt% ethanol solution of polyvinyl butyral previously placed in a reactor.

Separately, 100 ml of a $10^{-1}$ mol/l ethanol solution of tetramethylammonium bromide (Solution A) and 100 ml of a $10^{-1}$ mol/l ethanol solution of silver perchlorate (Solution B) were prepared in different containers. Suction ends of two roller pumps, RP-V$_2$ (made by Furue Science Co., Ltd.) were respectively connected to the container, and outlet ends of the roller pumps were introduced into the reactor. Firstly, Solution A was added to the reactor so as to adjust the silver potential (pAg) of the polymer solution to $-440$ mV (pAg: about 10.5). Then, Solution A and Solution B were simultaneously added to the polymer solution at a rate of 10 ml/min, during which time the addition rate was adjusted so that the silver potential of the reaction was maintained at $-440$ mV by increasing or decreasing the rate of rotation of the roller pump. Each solution was maintained at 35° C., and the reaction was conducted with stirring at a rate of 1,000 rpm. Electron microscopic evaluation of the thus-obtained silver bromide grains revealed that about 90% of the grains were within a particle size range of $0.1\mu \pm 0.03\mu$. Thus, monodisperse silver bromide grains were obtained.

COMPARATIVE EXAMPLE 1

Silver bromide grains were prepared in the same manner as in Example 1 except the adjustment of the addition rate for controlling the pAg was omitted. Electron microscopic evaluation of the thus-obtained silver bromide grains revealed that about 90% silver bromide grains had a particle size within the range of $0.03-0.25\mu$. Thus, the silver bromide grains had an extremely broad particle size distribution, and monodisperse silver bromide grains were not obtained.

COMPARATIVE EXAMPLE 2

The procedures of Example 1 were repeated and control of the pAg was attempted using a commercially available reference electrode, HS-205S (silver/silver chloride electrode made by Toa Denpa Co., Ltd.), in place of the reference electrode used in Example 1. However, the indicator of the potentiometer fluctuated so seriously that the pAg could not be accurately controlled. Thus, this pAg control resulted in no change in the particle size distribution of the silver bromide grains obtained from that obtained in Comparative Example 1.

EXAMPLE 2

Preparation of silver behenate using isopropanol as a reaction medium

A silver rod as an internal electrode 3, ceramic chips as a connector 4 and a bottom connector 5, an isopropanol solution of $10^{-2}$ mol/l of $AgClO_4$ and $10^{-1}$ mol/l of $Ca(NO_3)_2$ as an internal solution 2, and an isopropanol solution containing $10^{-1}$ mol/l of $Ca(NO_3)_2$ as an external solution 2' were used as in FIG. 1 to prepare a reference electrode.

This reference electrode was connected to a silver rod as a measuring electrode of a silver electrode via a potentiometer, HM-18B (made by Toa Denpa Co., Ltd.), as shown in FIG. 2, and the respective electrodes were immersed into 500 ml of a 2 wt% isopropanol solution of polyvinyl butyral.

Separately, 200 ml of a $10^{-1}$ mol/l isopropanol solution of ammonium behenate (Solution A) and 200 ml of a $10^{-1}$ mol/l is isopropanol solution of silver perchlorate (Solution B) were prepared in different containers. Suction ends of two roller pumps, RP-V$_2$ (made by Furue Science Co., Ltd.), were respectively connected to the containers, and outlet ends of the roller pumps were introduced into the reactor. Firstly, Solution A was added to the reactor so as to adjust the silver potential (pAg) of the polymer solution to $-300$ mV. Then, Solution A and Solution B were simultaneously added to the polymer solution at a rate of 20 ml/min, during which time the addition rate was adjusted so that the silver potential of the reaction solution was maintained at $-300$ mV (pAg: about 8.1) by increasing or decreasing the rate of rotation of the roller pump. Each solution was maintained at 50° C., and the reaction was conducted with stirring at a rate of 1,000 rpm.

Electron microscopic evaluation of the thus-obtained silver behenate revealed that about 90% of the grains had a longer-side length within the range of $0.3\mu \pm 0.1\mu$. Thus, monodisperse silver behenate grains were obtained.

COMPARATIVE EXAMPLE 3

Silver behenate grains were prepared in the same manner as in Example 2 except the adjustment of the rate of addition for controlling the potential of pAg was omitted. Electron microscopic evaluation of the thus-obtained silver behenate grains revealed that about 90% of grains had a longer-side length within the range of $0.1\mu$–$0.6\mu$. Thus, the resulting silver behenate grains had an extremely broad particle size distribution, and monodisperse silver behenate grains could not be obtained.

While the invention has been described in detail and with reference to specific embodiments thereof, it will be apparent to one skilled in the art that various changes and modifications can be made therein without departing from the spirit and scope thereof.

What is claimed is:

1. In a process for preparing slightly soluble silver salt grains by mixing a solution or dispersion of a silver salt-forming agent as a first liquid with a solution or dispersion of a silver ion-providing agent as a second liquid while controlling the electrode potential of the mixture of said first liquid and said second liquid using a measuring electrode and a reference electrode to produce said slightly soluble silver halide grains of specific characteristics depending upon the control of the electrode potential, the improvement which comprises said reference electrode comprising an internal electrode of a metal immersed in an internal solution of a metal salt of the metal of said internal electrode and an electrolyte, which metal salt and electrolyte do not release halide ions in the same liquid present as the major component in either of said first liquid or said second liquid.

2. The process of claim 1, wherein said first liquid and said second liquid contain one or more of an alcohol, a ketone, an aromatic hydrocarbon, an aliphatic unsaturated hydrocarbon, an ether, an ester or a cycloaliphatic hydrocarbon.

3. The process of claim 1, wherein said slightly soluble silver salt grains are silver halide grains.

4. The process of claim 1, wherein said slightly soluble silver salt grains are grains of an organic silver salt.

5. The process of claim 1, wherein the controlling of the electrode potential of the mixture is by controlling the pH.

6. The process of claim 1, wherein the controlling of the electrode potential of the mixture is by controlling the pAg.

7. The process of claim 1, wherein said internal electrode is silver, silver sulfide or silver oxide.

8. The process of claim 7, wherein the metal of the internal electrode is silver.

9. The process of claim 1, wherein the metal of the internal electrode is silver and wherein the metal salt of the metal of the internal electrode is a silver salt.

10. The process of claim 9, wherein said silver salt is a nitrate, a perchlorate, an acetate or a sulfate of silver.

11. The process of claim 10, wherein said metal salt of the metal of the internal electrode is silver nitrate or silver perchlorate.

12. The process of claim 1, wherein said electrolyte is a metal salt other than said metal salts of the metal of said internal electrode.

13. The process of claim 12, wherein said electrolyte is an alkali metal salt, an alkaline earth metal salt or an onium salt.

14. The process of claim 13, wherein said electrolyte is sodium nitrate, potassium nitrate, calcium nitrate or lithium nitrate.

15. The process of claim 11, wherein said metal salt of the metal of the internal electrode is silver perchlorate.

16. The process of claim 14, wherein said electrolyte is calcium nitrate.

17. The process of claim 2, wherein the organic liquid of said first liquid and the organic liquid of said second liquid have a boiling point of about 165° C. or less.

18. The process of claim 1, wherein said measuring electrode is a selective ion sensitive electrode.

19. The process of claim 18 above, wherein said selective ion sensitive electrode is a glass electrode.

20. The process of claim 18 above, wherein said selective ion sensitive electrode is a silver electrode.

* * * * *